US006808502B2

United States Patent
Nguyen

(10) Patent No.: US 6,808,502 B2
(45) Date of Patent: Oct. 26, 2004

(54) COMBINATION FINGER AND WRIST SPLINT

(76) Inventor: Jimmy Phong Xuan Nguyen, 81 Childs Road, Chipping Norton, New South Wales (AU), 2170

( * ) Notice: Subject to any disclaimer, the term of this patent is extended or adjusted under 35 U.S.C. 154(b) by 0 days.

(21) Appl. No.: 10/278,279

(22) Filed: Oct. 23, 2002

(65) Prior Publication Data
US 2003/0078531 A1 Apr. 24, 2003

(30) Foreign Application Priority Data
Oct. 23, 2001 (AU) ............................................. PR8401

(51) Int. Cl.[7] ............................................. A61F 5/00
(52) U.S. Cl. .............................. 602/21; 602/12; 602/22; 128/878
(58) Field of Search ............................ 602/5, 6, 12, 21, 602/22, 64; 128/878, 879; D24/190

(56) References Cited
U.S. PATENT DOCUMENTS

| | | | | | |
|---|---|---|---|---|---|
| 1,389,741 A | * | 9/1921 | Cotton | ......................... | 602/21 |
| 2,863,449 A | * | 12/1958 | Spencer | ........................ | 602/21 |
| 3,526,006 A | * | 9/1970 | Beardmore | .................. | 623/57 |
| 4,366,812 A | * | 1/1983 | Nuzzo | .......................... | 602/22 |
| 4,840,168 A | * | 6/1989 | Lonardo | ....................... | 602/22 |
| 5,058,576 A | * | 10/1991 | Grim et al. | ................... | 602/21 |
| 5,766,142 A | * | 6/1998 | Hess | ............................ | 602/22 |
| 5,772,620 A | * | 6/1998 | Szlema et al. | ................ | 602/21 |
| 5,947,915 A | * | 9/1999 | Thibodo, Jr. | ................... | 602/5 |
| 6,102,878 A | * | 8/2000 | Nguyen | ......................... | 602/5 |
| 6,261,253 B1 | * | 7/2001 | Katzin | .......................... | 602/21 |
| 6,293,918 B1 | * | 9/2001 | Wang | ........................... | 602/20 |
| 6,443,918 B1 | * | 9/2002 | Wang | ............................ | 602/5 |

* cited by examiner

Primary Examiner—Henry Bennett
Assistant Examiner—Amanda Flynn
(74) Attorney, Agent, or Firm—Jacobson and Johnson

(57) ABSTRACT

There is a mulifunctional finger, hand and wrist splint which includes a slab support member. In a position of use the slab support member extends along the underside of, and substantially follows the contours of, a wearer's lower forearm wrist and palm so that the wrist is immobilized. The slab support member in the area of the wearer's palm forms an anchor plate for a fracture support which is releasibly attached to the anchor at a range of positions to align with one or more finger or metacarpal fractures.

7 Claims, 3 Drawing Sheets

COMBINATION FINGER AND WRIST SPLINT

FIELD OF THE INVENTION

This invention relates to medical apparatus. More particularly it discloses an improved multifunction splint for treatment of fractures of fingers, metacarpal and wrist fractures. It can also be used to support the wrist in a neutral position that is required for carpal tunnel syndrome and post operative care of scaphoid, metacarpal fracture and wrist fracture.

BACKGROUND TO THE INVENTION

Splints currently used for setting finger fractures include those disclosed in the applicant's Australian patent application 21183/99. Such existing devices however cannot be adequately used to immobilize metacarpal, small hand joints (such as the scaphoid, lunate, hamate, triquetral, trapezoid, capitate, pisiform), or wrist fracture or to stabilize the wrist for treatment of carpal tunnel syndrome. Existing devices also do not offer mulifuctionality that can treat most fractures of the hand. For example, existing splints for 5th metacarpal fracture (commonly called boxer fracture) typically use plaster of paris/fiberglass to mould the shape of the palm and wrist in slight extension and the finger and palm in 90 degree flexion as this is the angle that allows maximum healing and minimal complication of joint stiffness. It is even more difficult to treat a fracture of 4th, 3rd or 2nd metacarpal fractures as it is often very difficult technically to stabilize the carpal-metacarpal joint in isolation by using plaster of paris and aluminum strip supports to hold the finger in 90 degree flexion. Therefore surgery is often contemplated. Furthermore the use of such existing splints is time consuming and often requires a doctor or physiotherapist to apply them. Such splints can often cause allergies due to sweating of the skin. In circumstances such as the sport field or in war zones it is desirable to have a splint that can be easily and quickly applied to stabilize any finger, metacarpal, or wrist fracture of either left or right hand. Other disadvantages of using molded splints such as those of plaster of paris is that they must be worn for the duration of the treatment which is usually 4 to 6 weeks. Therefore joint stiffness, allergies and unpleasant odors often result. It is also considered by some medical practitioners that allowing the finger or wrist to be easily moved for active mobilization, at least once or twice per day during the treatment period achieves better bone healing and reduces complications from stiffness and skin allergies. This is not feasible with existing splints.

SUMMARY OF THE INVENTION

It is an object of this invention to ameliorate the aforementioned disadvantages and accordingly a combination mulifunctional finger, hand and wrist splint is disclosed, said splint including a slab support member which in a position of use extends along the underside of and substantially follows the contours of, a wearer's lower forearm, wrist and palm whereby the wrist is immobilized in extension and said slab support member in the area of the palm forms an anchor plate for a finger support which is releasibly attached to said anchor plate at any one of a range of positions to align with one or more finger or metacarpal fractures.

BRIEF DESCRIPTION OF THE DRAWINGS

The currently preferred forms of this invention will now be described with reference to the attached drawings in which.

DETAILED DESCRIPTION OF THE PREFERRED EMBODIMENTS

Figure 1:
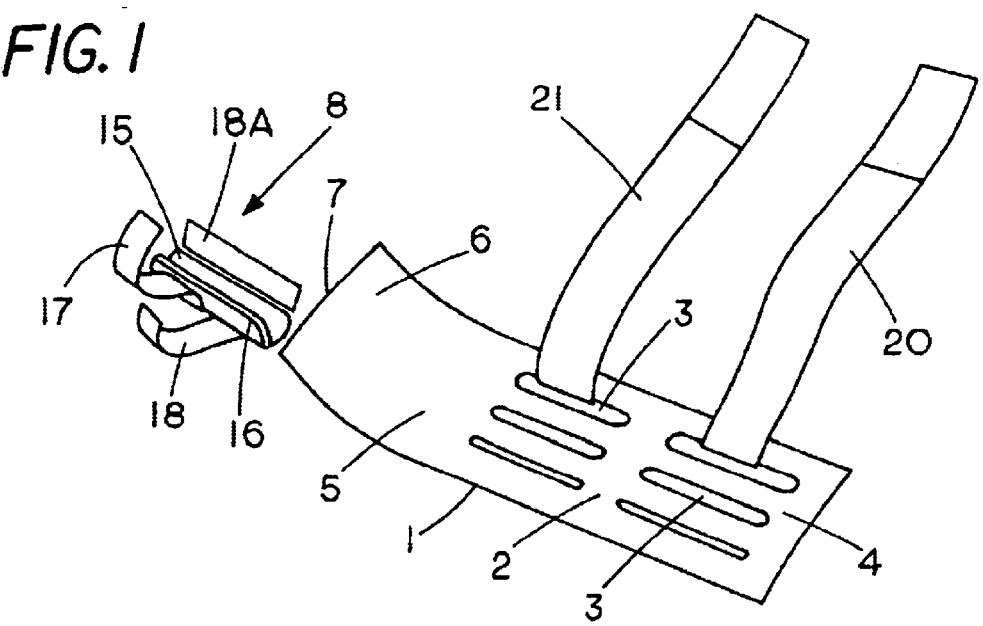
FIG. 1 shows an upper side perspective view of a splint according to a first embodiment of the invention.
Figure 2:
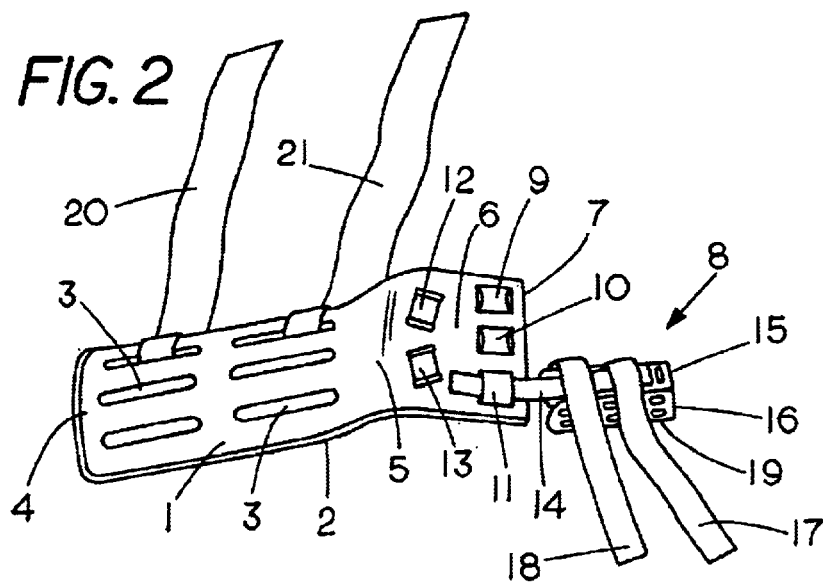
FIG. 2 shows an underside perspective view of the splint of FIG. 1, FIGS. 3 and 4 show perspective views of the splint fitted to a wearer's wrist and finger.

Referring first to FIGS. 1 and 2 the splint is adapted to fit either arm and may comprise a one piece slab support member constructed from a shape retaining sheet material 1 such as plastic or aluminium which is nevertheless able to be contoured to closely fit the wearer's forearm, wrist and palm. The inside of the support member is lined with a soft foam material 2 or the like and there are ventilation slots 3 for comfort against the wearer's skin. One end portion 4 of the support member is rounded to cradle the forearm. It merges into a central section 5 which abuts the heel of the hand and supports the wrist at an inclination with this embodiment of about 30 degrees. This invention however is not limited to this angle.

The opposite end portion of the support member forms an anchor plate 6 which abuts the wearer's palm. The edge 7 of the plate may be squared off and a number of sockets provided adjacent to said edge which allow the finger support 8 to be fitted at different positions 9, 10, and 11, depending upon the finger to be immobilized. There are also laterally directed sockets 12 and 13 for the left and right thumbs. While the embodiment shown is provided with only five socket positions for the fingers and thumbs additional positions may be provided according to design preference.

The finger support 8 preferably comprises a strip 14 of aluminium or other reasonably stiff yet pliable material which is adapted at one end for a close tolerance push fit into a selected one of the sockets. The strip 14 at the other end mounts an elongated channel 15 with hinged side panels 16 to cradle the wearer's finger or thumb. There are also velcro fasteners 17, 18 fitted to the underside of the channel which may be tightened to close the panels around the finger and immobilize it. The inside of this channel 15 is preferably also preferably lined with soft foam 18A and there are ventilation slots 19 for comfort. The angle at which the fracture is immobilized can be adjusted by bending the strip 14.

Figure 3:
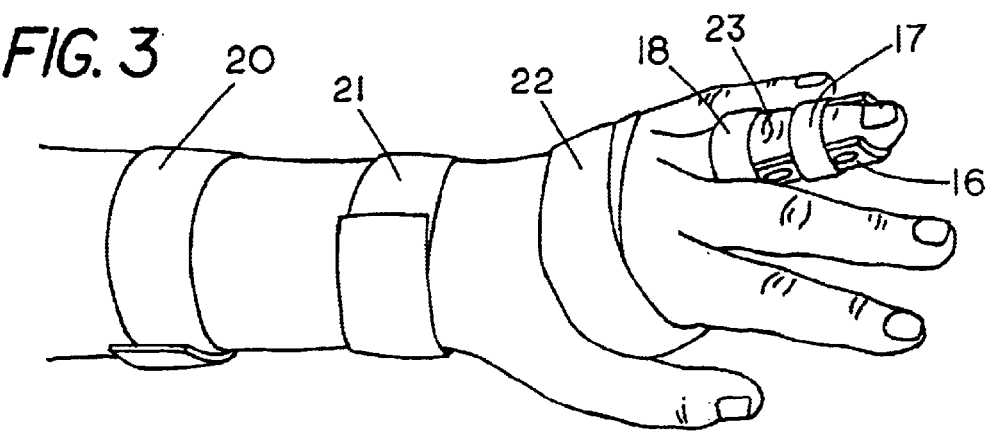
Figure 4:
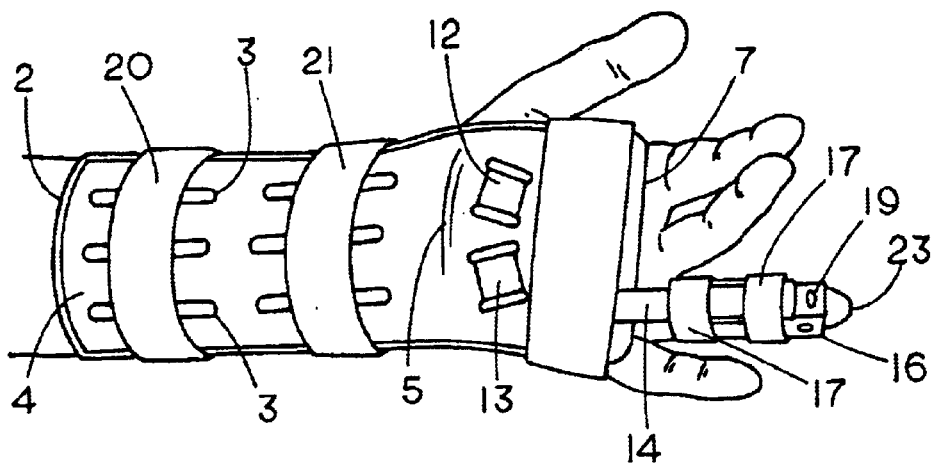

As shown in FIGS. 3 and 4 the slab support member 1 is attached to the wearer's forearm and hand by means of VELCRO® straps 20, 21 and 22. While in this case the ring finger 23 is being immobilized the finger support 8 could alternatively be inserted into any of the sockets for fractures of the other fingers or thumb.

With the second and third embodiments of the invention the components of the splint shown which correspond in function to those of FIGS. 1 to 4 are indicated by the same numbers which are primed (') and (") to distingush them.

Figure 5:
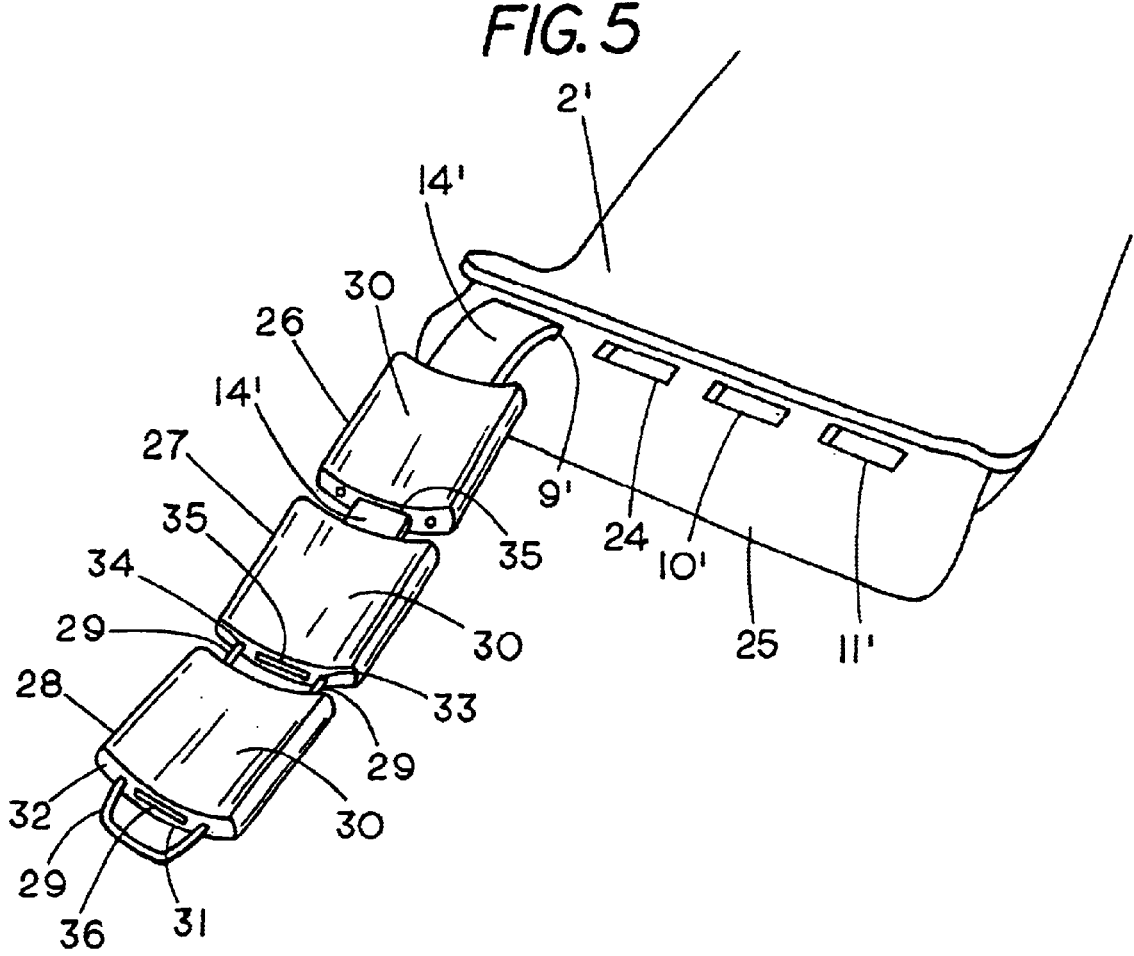
FIGS. 5 and 6 show part of a splint according to a second embodiment of the invention.

Referring FIG. 5 there is an additional forward directed socket 24 formed in the support member to provide for each finger position. The end of the support member is also rounded to form a lip 25.

The connector strip 14' is shown fitted into socket 9' which would correspond to a wearer's left hand index finger.

The digit splint fitted comprises a set of three segments 26, 27 and 28 which are arranged on a connecting linkage formed by a U shaped metal wires 29 and the aforementioned connector strip 14'. Preferably the segments are identical in shape with each having a concave upper surface 30, rounded underside and planar ends 31, 32 through which three apertures 33, 34 and 35, pass. These apertures are spaced symmetrically about the center-lines of each segment and extend completely through the length thereof. The central rectangular apertures 35 in segments 26 and 27 are shaped to receive the connecting strip 14' as a close tolerance push fit. The other apertures 33 and 34 receive the wires 29 which pass through segments 27, 28. The assembly is thus longitudinally adjustable but resistant to lateral deflection. The length of the digit splint can be easily and quickly adjusted by the practitioner without the aid of tools.

Figure 6:
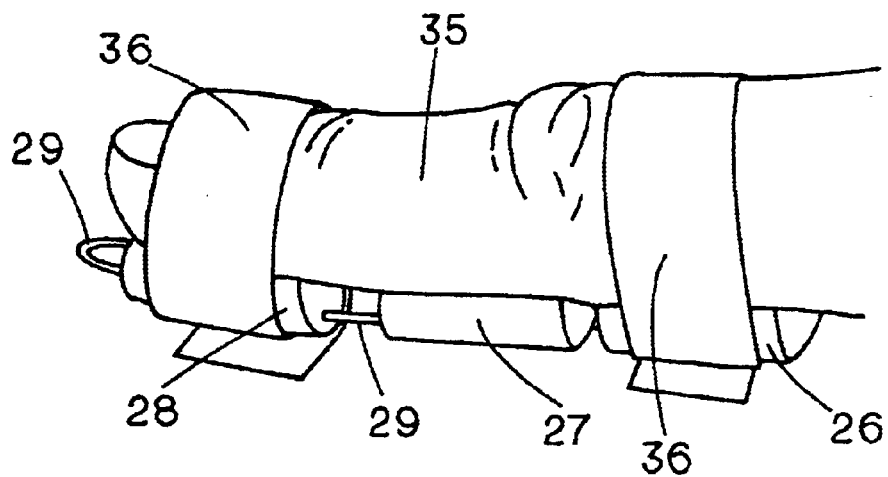

As shown in FIG. 6 the splint, after adjustment for length, is fitted with the segment surfaces 30 engaging along the underside or dorsal surface of an injured finger 35. Preferably the splint is held in place by VELCRO® straps 36 or the like. As mentioned earlier the upper surfaces 30 of the segments are preferably concave so as to follow the contour of the dorsal surface and cradle the finger.

The finger shown in FIG. 6 is held straight as is required for some phalangeal fractures. The malleable nature of the mild steel wires 29 and connecting strip 14' used with this embodiment however enables the splint to be bent so as to alternatively put the finger in flexion or in extension as required for mallet finger injuries. In the latter case the splint would also be modified from the example shown to use only two segments to hold the distal phalangeal joint in extension.

Figure 7:
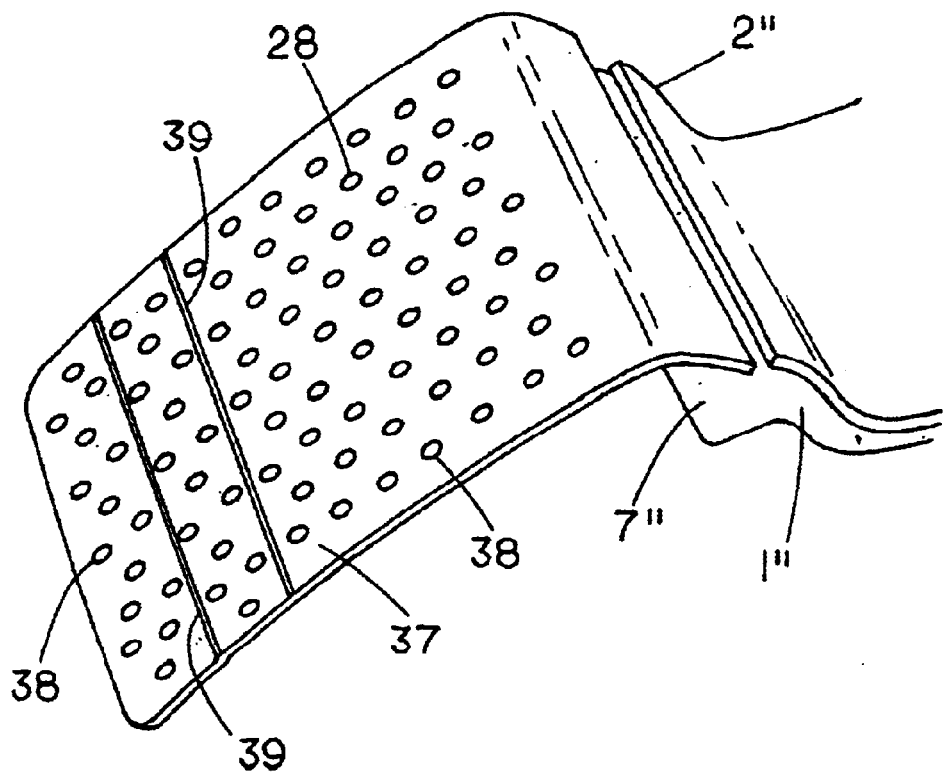
FIG. 7 shows part of a splint according to a third embodiment of the invention.

As an alternative to the digital splint and in accordance with a third embodiment of the invention a multiple finger support plate 37 could be fitted as shown in FIG. 7 using the connecting strips referred to earlier. The support plate would simultaneously immobilize two or fingers. There are ventilations holes 38 distributed over the surface of the plate and transverse notches 39 are provided to assist cutting the plate to suit the wearers requirements.

It will thus be appreciated that this invention at least in the form of the embodiments disclosed provide a novel and low cost adjustable splint for finger, metacarpal and wrist fractures. The advantages of a splint according to this invention include the following:

- practical
- multifunctional
- water resistant
- non allergic
- can be easily applied in emergencies without assistance of medical personnel
- provides immobilization of finger joints, small joints of the hand and wrist to minimise pain and discomfort
- provides better and easier immobilization of thumb and all other digits due to multiple slot adaptability
- can immobilize any joint fracture from the tip of the finger to the distal aspect of the forearms
- allows the finger to immobilize at variable angles with better stabilization at the wrist joint
- suitable for post operative care of hand or wrist surgery
- VELCRO® strapping allows the splint to be removed and reapplied easily for early active mobilization of joints
- removal of the splint is simple and painless as no adhesive or plaster of paris is used and hence no cutting equipment is required
- increased comfort reduces patient resistance to full term use of the splint.

Clearly however the examples described are only the currently preferred forms of the invention and a wide variety of modifications may be made which would be apparent to a person skilled in the art. For example the shape and configuration of the slab support member and the means of attaching the fracture support thereto may be changed according to design preference. The slab support may also be made extendible to suit different sizes of forearm. Finally, while a low cost and easily molded plastic is currently preferred the invention at this stage is not restricted to the use of any specific materials as this is to be the subject of further research by the inventor.

What is claimed is:

1. A multifunctional finger, hand and wrist splint having a slab support member which in a position of use extends along the underside of, and substantially follows the contours of, a wearer's lower forearm wrist and palm whereby the wrist is immobilized and said slab support member in the area of the wearer's palm forming an anchor for a digit splint having a plurality of segments which are arranged end-to-end on a connecting linkage formed by metal wires and a connector strip whereby the assembly is longitudinally adjustable but resistant to lateral deflection, said digit splint releasably attached to said anchor at a range of positions to align with one or more finger or metacarpal fractures wherein the digit splint is attached to the anchor by a connector strip which fits into sockets in said anchor, said connector strip made from a pliable material whereby the angle at which the digit splint is attached to the anchor can be adjusted by bending said strip.

2. The multifunction finger, hand and wrist splint as claimed in claim 1, wherein the digit splint includes an elongated channel with hinged side panels.

3. The splint as claimed in claim 1 wherein the segments are identical in shape with each segment having a concave upper surface a rounded underside and planar ends through which apertures are formed to receive said metal wires and connector strip.

4. The splint as claimed in claim 3 wherein there are three segments arranged end-to-end to form opposite end segments and a center segment with said metal wires and connector strip extending through respective opposite ones of said end segments and into said center segment.

5. The splint as claimed in claim 1 wherein the digit splint is bendable so as to put a finger fracture in flexion or in extension as is required for mallet fracture injuries.

6. The splint as claimed in claim 5 wherein the fracture support is a multiple finger support plate able to simultaneously immobilize two or more fingers.

7. The splint as claimed in claim 6 wherein a central section thereof abuts the heel of the wearer's hand and supports the wearer's wrist at an angle of about 30 degrees.

* * * * *